United States Patent [19]

Lassila

[11] Patent Number: 5,760,275
[45] Date of Patent: Jun. 2, 1998

[54] CYANOACETALS BY HYDROFORMLATION OF UNSATURATED NITRILES IN THE PRESENCE OF ORTHOESTERS

[75] Inventor: Kevin Rodney Lassila, Macungie, Pa.

[73] Assignee: Air Products and Chemicals, Inc., Allentown, Pa.

[21] Appl. No.: 803,173

[22] Filed: Feb. 19, 1997

[51] Int. Cl.$^6$ .................................................. C07C 255/03
[52] U.S. Cl. ........................................... 558/353; 558/410
[58] Field of Search ........................................ 558/353, 410

[56] References Cited

U.S. PATENT DOCUMENTS

| | | | |
|---|---|---|---|
| 2,506,571 | 5/1950 | Latrell et al. | |
| 3,242,203 | 3/1966 | Noyori et al. | 260/465.1 |
| 3,337,603 | 8/1967 | Kato et al. | 260/465.1 |
| 3,466,317 | 9/1969 | Kuper et al. | |
| 3,579,562 | 5/1971 | Weigert et al. | 260/465.1 |
| 4,235,744 | 11/1980 | Pesa et al. | 252/428 |
| 4,238,357 | 12/1980 | Pesa et al. | 252/431 N |
| 4,299,771 | 11/1981 | Garrou. | |
| 4,299,777 | 11/1981 | Garrou et al. | 260/465.6 |
| 4,313,893 | 2/1982 | Pesa et al. | 260/465.4 |
| 4,344,896 | 8/1982 | Kurkov | 260/465.1 |
| 4,451,407 | 5/1984 | Pesa. | |

*Primary Examiner*—C. Warren Ivy
*Assistant Examiner*—Jean F. Vollano
*Attorney, Agent, or Firm*—Russell L. Brewer

[57] ABSTRACT

Disclosed is an improved process for producing cyanoaldehydes and acetals wherein an α, β-unsaturated nitrile is reacted with carbon monoxide and hydrogen in the presence of a Group 8 metal catalyst. The improvement in the hydroformylation process resides in effecting the reaction in the presence of a trialkyl orthoester [(R'O)$_3$CR"] or a dialkyl ketal [(R'O)$_2$CR"$_2$].

13 Claims, No Drawings

CYANOACETALS BY HYDROFORMLATION OF UNSATURATED NITRILES IN THE PRESENCE OF ORTHOESTERS

BACKGROUND OF THE INVENTION

There is substantial literature pertaining to the preparation of cyanoaldehydes and acetals, particularly cyanopropionaldehyde acetals by the Group 8 metal catalyzed hydroformylation reaction of an α,β-unsaturated nitrile with carbon monoxide and hydrogen, the acetals being formed in situ or subsequent to the formation of the aldehyde by reaction with an alcohol.

Cyanopropionaldehyde dimethyl acetal is the predominant cyanopropionaldehyde alkyl acetal of interest and it is useful as a precursor to aminobutyraldehyde dimethyl acetal, a component in formaldehyde-free crosslinker systems. It is also useful as a selective solvent for separation of hydrocarbons, as an intermediate for the preparation of pharmaceuticals and dyestuffs, and as a pest control agent.

The following patents are illustrative of the catalytic processes for producing cyanoaldehydes and cyanoaldehyde alkyl acetals.

U.S. Pat. No. 2,506,571 discloses a process for the preparation of cyanopropionaldehyde alkyl acetals by the cobalt-catalyzed hydroformylation of acrylonitrile in the presence of at least two moles of an alkanol at temperatures of 100°–200° C. and at pressures of at least 8800 psig. A small amount of t-butyl catechol or similar compound is added to inhibit acrylonitrile polymerization. After 8 hours, cyanopropionaldehyde alkyl acetals are produced in 32% yield.

U.S. Pat. No. 3,337,603 discloses a continuous process for the preparation of cyanopropionaldehyde alkyl acetals by the cobalt-catalyzed hydroformylation of acrylonitrile at pressures from 1500 to 4500 psi. Yields of over 80% were obtained.

U.S. Pat. No. 3,466,317 discloses a process for producing cyanopropropionaldehyde alkyl acetals at relatively low pressures (but at least 880 psi) by reacting acrylonitrile, methanol, carbon monoxide and hydrogen in the presence of a Group VIII metal-containing hydroformylation catalyst and in the presence of an acid catalyst.

U.S. Pat. No. 4,299,777 discloses a process for the preparation of cyanopropropionaldehyde alkyl acetals by the reaction of an alcohol with acrylonitrile, CO and hydrogen in the presence of $Co_2(CO)_8$. A cyanoalkyl amine such as imino diacetonitrile is added as a promoter to enhance selectivity to the cyanopropropionaldehyde alkyl acetals.

U.S. Pat. No. 4,238,357 discloses the formation of cyanopropionaldehyde alkyl acetals as a byproduct in the reaction of acrylonitrile with carbon monoxide in the presence of a catalyst comprised of cobalt or ruthenium carbonyl and a promoter such as a heterocyclic nitrogen compound or a phosphorous or sulfur oxide.

U.S. Pat. No. 4,235,744 is directed to the formation of esters, aldehydes, and amides. The addition of a polyamine promoter ligand such as tetramethyl-1,3-propane diamine results in enhanced selectivity to branched carbonylation products such as methyl-α-cyanopropropionate. Cyanopropionaldehyde alkyl acetal is formed as a byproduct.

U.S. Pat. No. 4,344,896 discloses the preparation of 2-cyanoaldehydes by the rhodium-catalyzed hydroformylation of α,β-unsaturated nitrites such as acrylonitrile, methacrylonitrile and ethylacrylonitrile in the presence of a catalyst comprising a rhodium complex in combination with carbon monoxide and a triorgano compound of phosphorus, arsenic or antimony ligand. Triphenylphospite is a preferred ligand.

U.S. Pat. No. 3,579,562 discloses the hydroformylation of unsaturated esters or nitriles, e.g., methacrylic acid esters and nitriles, in the presence of a rhodium catalyst, e.g., rhodium oxides and salts capable of forming rhodium carbonyls under the hydroformylation conditions.

U.S. Pat. No. 3,242,203 discloses a process for forming cyanopropionaldehyde by reacting acrylonitrile in an oxo reaction wherein the reaction is carried out in presence of a solvent which can dissolve the cyanopropionaldehyde reaction product. Solvents employed in the reaction include hydrocarbons having a boiling point of from 28° to 330° C., alcohols, etc. Cobalt carbonyl is employed as a catalyst with hydroquinone being used to inhibit polymerization.

U.S. Pat. No. 4,313,893 discloses a process for the carbonylation of olefinically unsaturated compounds by contacting such olefinically unsaturated compounds with carbon monoxide and a compound containing a replaceable hydrogen atom in the presence of a catalyst comprising cobalt or ruthenium carbonyl and a promoter ligand selected from heterocyclic nitrogen compounds and phosphorus or sulfur oxides. Representative olefinically unsaturated compounds include acrylonitrile and allyl alcohol. Representative promoter ligands include picoline oxide, pyridine oxide, triethyl and triphenylphospine oxide, and so forth.

BRIEF SUMMARY OF THE INVENTION

This invention relates to an improved process for producing cyanoaldehydes and acetals wherein an α,β-unsaturated nitrile is reacted with carbon monoxide and hydrogen in the presence of a Group 8 metal catalyst. The improvement in the hydroformylation process resides in effecting the reaction in the presence of a trialkyl orthoester [(R'O)₃CR"] or a dialkyl ketal of the formula [(R'O)₂CR"₂].

Addition of the orthoester or ketal to the hydroformylation process can result in the following advantages:

- an ability to obtain excellent yields of cyanopropionaldehyde alkyl acetals;
- an ability to obtain high yields of cyanopropionaldehyde acetal products under mild reaction conditions;
- an ability to effect reaction under conditions of high unsaturated nitrile loading (i.e., acrylonitrile concentration) resulting in efficient reactor utilization;
- an ability to maintain high yields of cyanopropionaldehyde acetal product when the reaction is performed under conditions of high acrylonitrile loading concentration; and,
- an ability to obtain high rates of production of cyanopropionaldehyde acetals using mild reaction conditions and catalyst levels.

BRIEF DESCRIPTION OF THE SEVERAL VIEWS OF THE DRAWINGS

Not Applicable

DETAILED DESCRIPTION OF THE INVENTION

The process described is an improvement in the conventional hydroformylation of unsaturated nitrites to produce cyanoaldehydes and cyanoaldehyde alkyl acetals, and particularly cyanopropionaldehyde alkyl acetals. Nitriles suitable for use in the hydroformylation reaction include α,β- unsaturated nitrites such as acrylonitrile and alkyl- and aryl-substituted acrylonitriles. Examples include acrylonitrile, 2-methylacrylonitrile, 2-n-propylacrylonitrile, 2-ethylacrylonitrile, 2-isopropylacrylonitrile and 2-phenyl-acrylonitrile.

To produce the acetal from the aldehyde, an alcohol is incorporated into the reaction. One can convert the aldehyde to the acetal either in situ or subsequent to its formation. Alcohols conventionally employed in the hydroformylation of unsaturated nitriles and employed herein include alkyl, cyclooalkyl and aryl alcohols or combinations thereof. The total number of carbon atoms can range from about 1–30 but preferably the carbon atom range for the alcohol is from 1–8. Also, it is preferable that these alcohols are primary or secondary alcohols. Examples of suitable alcohols include methanol, ethanol, isopropyl alcohol, butanol, butan-2-ol; 3-hexanol, ethyldodecanol, ethylene glycol, propylene glycol, cyclohexanol, octanol 2-phenyl -6-nonanol, and so forth.

The nitrile is added to the reactor in an amount to provide about 5 to 60 weight percent of the organic components or reactants and preferably from 20 to 35 weight percent of the organic components or reactants employed in the process.

A key to the improved process resides in the incorporation of a trialkyl orthoester or dialkyl ketal in the reaction. A number of orthoesters are applicable and these include trialkyl orthoesters of aromatic or aliphatic carboxylic acids. Specific examples are trimethylorthoformate, triethylorthoformate, tri-n-propylorthoformate, tri-i-propylortho-formate, tri-n-butylorthoforrmate, tri-sec-butylorthoformate, tri-i-butylorthoformate, and so on. In addition to these orthoesters of formic acid, the corresponding orthoesters of acetic, propionic, and other branched or unbranched aliphatic carboxylic acids may be used. Similarly, the orthoesters of aromatic carboxylic acids such as benzoic acid or substituted benzoic acids or other aromatic carboxylic acid are applicable. Benzoic acids may be substituted with $C_{1-8}$ alkyl, $C_{1-4}$ alkoxy, and pendent groups which are inert, ie., which do not interfere with the hydroformylation of the unsaturated nitrile. In general the orthoesters contemplated as useful in this invention are those derived from carboxylic acids having generally from 1 to 8 carbon atoms and alcohols having from 1 to 8 carbon atoms. However, the preferred orthoesters are the reaction products of formic acid and lower alkanols, e.g. the $C_{1-4}$ alkanols.

The invention can also be practiced with dialkyl ketals in place of or in combination with the orthoester. Suitable dialkyl ketals include those prepared by reaction of a ketone in the presence of a suitable catalyst with a $C_{1-8}$ alcohol such as methanol, ethanol, n-propyl alcohol, isopropyl alcohol, n-butyl alcohol, sec-butyl alcohol, and so on. Ketones suitable for preparation of the ketals include dialkyl-, diaryl-, and alkylaryl ketones. Specific examples include acetone, 2-butanone, 2-pentanone, methylisobutylketone, acetophenone, benzophenone, and the like. Ketones containing aryl groups may contain inert substituents.

In a system using an alcohol solvent, the alcohol and the orthoester or ketal should be chosen so that the alkoxy group of the orthoester or ketal and the alcohol are matched; if different alkoxy groups are used, a mixture of cyanoacetals containing all of the alkoxy substituents may be produced.

The level of orthoester should be sufficient to produce a beneficial effect in the formation of cyanoacetals. Generally a range from about 0.5 to 1.5 moles per mole of α,β unsaturated nitrile is effective, and a range from about 0.9 to 1.1 moles orthoester to nitrile is preferred. The reaction chemistry shows the stoichiometry to be about 1:1. However, in systems containing both an orthoester or ketal, and an alcohol, significantly less than one equivalent of orthoester or ketal may be employed, e.g., a 0.1:1 level, because the increased level of intermediate cyanoaldehyde byproduct can be converted to the acetal by reaction of the intermediate aldehyde with the alcohol.

The catalysts suitable for use in the hydroformylation include those Group 8 metals such as cobalt, ruthenium and rhodium containing catalysts conventionally used for the hydroformylation of unsaturated nitrites. Especially suited are the cobalt catalysts which are capable of converting to the carbonyl and these include dicobalt octacarbonyl and hydridocobalt tetracarbonyl. Ligand promoters may also be included in the reaction medium. Examples include phosphines and phosphine oxides, pyridine and pyridine oxides, sulfoxides, arsines and so forth. Other examples of catalysts and levels of incorporation are set forth in the background of the invention and these catalysts are incorporated by reference. The catalyst may be preformed, or it may be formed in situ as is known in the art. The catalyst is incorporated into the reaction in an amount from about 0.05 to 5 percent by weight based upon total organic charge on a contained metal basis. Preferably, the concentration should be 0.1 to 1 percent by weight. Use of too low a level of catalyst may result in long reaction times or ineffective reaction, whereas use of too high a level of catalyst may adversely affect the economics of the process and may result in the separation of free metal from the reaction mixture.

In effecting the hydroformylation the synthesis gas should have a hydrogen/carbon monoxide molar ratio within a range of 0.5 to 2:1 preferably 0.9 to 1.1:1 and most preferably about 1:1. The use of synthesis gas having a hydrogen/carbon monoxide molar ratio other than 1:1 is possible, although in many cases the composition of the gas will be different than that required by the stoichiometry of the reaction, possibly resulting in the depletion of the minor component as the reaction proceeds. Such synthesis gas mixtures are common in hydroformylation processes.

The reaction should be run at a temperature sufficient to provide a convenient reaction rate, but low enough to prevent thermal decomposition of the reagents, products, or the hydroformylation catalyst. Temperatures from about 40° C. to about 150° C. are preferred, especially temperatures from 60° to 120° C. Below these temperatures, the rate of reaction is inconveniently low, whereas above these temperatures, decomposition of the product begins to occur.

The reaction can be run at a pressures from about 100 psig to about 5000 psig, preferably about 400–1200 psig and most preferably from about 700–800 psig.

The reaction chemistry for the process of this invention is represented as follows, where the reaction is illustrated for a trialkyl orthoester:

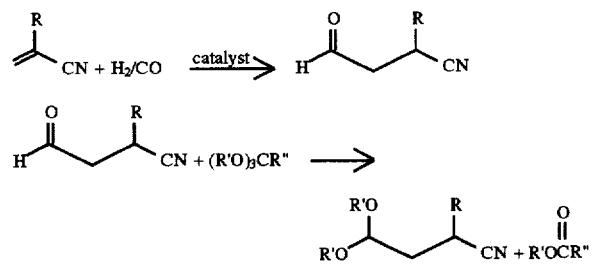

wherein R is hydrogen, $C_{1-8}$ aliphatic or aromatic, R' is aliphatic having from 1 to 8 carbon atoms, and R" is hydrogen, $C_{1-8}$ aliphatic or aromatic.

For hydroformylation reactions in the presence of a dialkyl ketal, the second step of the reaction can be illustrated as follows:

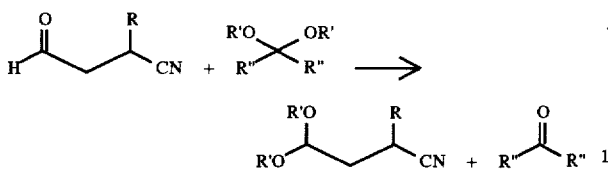

wherein R, R', R" are the same as above except that R" cannot be hydrogen.

By performing the hydroformylation of acrylonitrile in the presence of an appropriate quantity of a trialkylorthoester or a dialkyl ketal, yields of cyanopropionaldehyde acetals can be as high as 80% and possibly higher while the reaction time may be approximately halved under reaction conditions which are, in all other respects, identical to those used in prior art procedures.

The following examples illustrate the limitations of the art and the benefits which can be obtained by application of this invention.

COMPARATIVE EXAMPLE 1

Preparation Of Cyanopropionaldehyde Dimethyl Acetal At Low Pressure

This example illustrates a conventional procedure for the preparation of cyanopropionaldehyde dimethyl acetal at pressures slightly lower than conventionally used in the prior art. A 1 L autoclave was charged with methanol (493 g), acrylonitrile (63.0 g), and $Co_2(CO)_8$ (3.6 g). This reactor charge had a volume of 700 mL, corresponding to approximately 70% of the reactor volume. The reactor was sealed, purged and pressure checked with nitrogen, and then purged and pressure checked with a 1:1 $H_2$:CO mixture. The reactor was pressured to 500 psig with 1:1 $H_2$:CO and heated to 90° C. When the temperature had reached 90° C., the pressure was increased to 720 psig where it was maintained by means of a regulated ballast. After about 7 hours, gas uptake had ceased and the reactor contents were cooled to ambient temperature and removed from the reactor. Analysis by internal standard gas chromatography showed that 105 grams of cyanopropionaldehyde dimethyl acetal were contained in the reactor, making the yield of cyanopropionaldehyde alkyl acetal 69% based on moles of acrylonitrile.

COMPARATIVE EXAMPLES 2–4

Cyanopropionaldehyde Dimethyl Acetal At Various Acrylonitrile Concentrations Examples 2–4 illustrate attempts to increase reactor productivity by running at higher acrylonitrile concentrations than conventionally used and used in Example 1. The reactions were performed in a manner similar to that of Comparative Example 1, except that the amount of the acrylonitrile was increased to the amounts set forth in Table 1. The amount of methanol was decreased by the amount required to maintain a constant reagent volume of 700 mL. The results of Examples 1–4 are summarized in Table 1.

TABLE 1

Effect of Increased Acrylonitrile Concentration On Hydroformylation Reaction[a]

| Example | Acrylonitrile conc.[b] | time[c] | k[d] | Gas Uptake[e] | CPA grams[f] | CPAA grams[f] | Yield[9] CPA | Yield CPAA[9] |
|---|---|---|---|---|---|---|---|---|
| 1 | 63.0 | 7.3 | 280 | 96.0 | 2.7 | 105.3 | 3.9 | 69 |
| 2 | 69.3 | 12.5 | 250 | 95.6 | 6.2 | 104.5 | 5.7 | 62 |
| 3 | 75.6 | 13.5 | 250 | 93.4 | 21.7 | 72.3 | 18.3 | 39 |
| 4 | 81.9 | 16.0 | 330 | 97.8 | 25.3 | 46.5 | 19.7 | 23 |

[a]3.6 g $Co_2(CO)_8$ (0.22 wt % Co), 90° C., 720 psig 1:1 $H_2$:CO, MeOH plus acrylonitrile total volume 700 ± 5 mL.
[b]Grams.
[c]Time required for gas uptake to cease, hours.
[d]Mmol of acrylonitrile converted per hour at maximum uptake rate.
[e]Percent of theoretical.
[f]Grams; by internal standard GC analysis.
[9]Molar percent based on acrylonitrile introduced.

Table 1 shows that CPAA yields decrease significantly with increased acrylonitrile concentration and the decrease in yield is sufficient to negate the effect of any potential enhancement in reactor productivity due to the use of more acrylonitrile. That increased productivity to CPAA was not obtained with increased acrylonitrile loading can be seen by observing that the weight of CPAA formed in the reactor batch. The weight of CPAA actually decreased when higher reactor loadings of acrylonitrile were used. Although the amount of CPA increased with an increased acrylonitrile loading, conversion of CPA to CPAA would require an additional step. It is also important to note, that in addition to less effective reactor utilization on a per batch basis, reaction times increased dramatically with increased acrylonitrile concentration, further contributing to diminished reactor productivity.

EXAMPLE 5

Hydroformylation Of Acrylonitrile In The Presence Of An Orthoester

This example illustrates the hydroformylation of acrylonitrile in the presence of an orthoester. A 1 L autoclave was charged with acrylonitrile (63.0 g), methanol (389.9 g), trimethylorthoformate (126.1 g), and $Co_2(CO)_8$ (3.6 g). These amounts correspond to the addition of one molar equivalent of the orthoester based on acrylonitrile while maintaining the reagent volume in the reactor at a constant level of 700 mL, ie., approximately 70% as in Comparative Examples 1–4. Other than these changes, the hydroformylation was performed using the procedures and reaction conditions of Comparative Example 1.

Gas uptake was complete in 2.7 h compared to 7.3 h using the procedure of Example 1. Furthermore, the amount of CPAA produced in the reactor batch increased to 125 g compared to 105 g using the method of Example 1, and the molar yield based on acrylonitrile increased to 82% compared to 69%. These results demonstrate that the addition of an orthoester increases the amount of cyanopropionaldehyde dimethyl acetal which can be produced in a given reactor volume in a given amount of time by producing the desired product in higher yield and in a shorter period of time.

EXAMPLES 6–8

Hydroformylation Of Acrylonitrile In The Presence Of An Orthoester

These examples compare the effect of acrylonitrile concentration when the reaction is carried out in the presence of an alkyl orthoester. Examples 1-4 illustrated that in the absence of an orthoester, addition of larger amounts of acrylonitrile led to diminished productivity of cyanopropionaldehyde dimethyl acetal. The hydroformylation reactions were performed in a manner similar to that of Example 5 using the acrylonitrile amounts given in Table 2. With an increase in acrylonitrile loading, there was a corresponding increase in TMOF loading to maintain a 1:1 molar equivalent TMOF/acrylonitrile ratio and a corresponding decrease in methanol loading to maintain a constant reagent volume of 700 mL. The results of Examples 5–8 are set forth in Table 2.

EXAMPLE 9

Hydroformylation Of Acrylonitrile In The Presence Of An Orthoester And In The Absence of Methanol This example illustrates the effect of methanol removal from the reactor, the objective being to provide for a high concentration of acrylonitrile and thereby form a maximum quantity of cyanopropionaldehyde dimethyl acetal per reactor batch. To a 1 L autoclave was charged acrylonitrile (212.3 g), trimethylorthoformate (424.6 g), and $Co_2(CO)_8$ (3.6 g). The volume of reagents was again 700 mL as in the earlier examples. The reactor was sealed, purged, and pressure-checked and the hydroformylation was performed at 90° C. and 720 psig. The conditions and results are shown in Table 3.

TABLE 3

| Example | Acrylonitrile conc[b] | time[c] | $k^d$ const | gas uptake[e] | CPAA grams | Yield[f] CPAA | (CPA) |
|---|---|---|---|---|---|---|---|
| 9 | 212.3 | 15.3 | 580 | 119 | 322 | 62 | (15) |

[a]3.6 g $Co_2(CO)_8$ (0.22 wt % Co), 90° C., 720 psig, 1:1 $H_2$:CO, Total reagent volume 700 ± 5 mL.
[b]Grams.
[c]Time at temperature for gas uptake to cease, hours.
[d]mmol acrylonitrile converted per hour at maximum uptake.

TABLE 2

Formation of Cyanopropionaldehyde Acetals in the Presence of Orthoesters

| Example | Acrylonitrile conc.[b] | time (h) | $k^d$ const | gas uptake[e] | CPAA grams | Yield[f] CPAA | (CPA) |
|---|---|---|---|---|---|---|---|
| 5 | 63.0 | 2.7 | 530 | 98 | 125 | 82 | (—) |
| 6 | 69.3 | 3.0 | 500 | 97 | 136 | 80 | (—) |
| 7 | 75.6 | 3.3 | 560 | 102 | 150 | 81 | (—) |
| 8[a] | 81.9 | 4.0 | 500 | 103 | 156 | 79 | (—) |
| 8[b] | 81.9 | 3.7 | 530 | 100 | 160 | 80 | (—) |

[a]3.6 g $Co_2(CO)_8$ (0.22 wt % Co), 90° C., 720 psig, 1:1 $H_2$:CO, Total reagent volume 700 ± 5 mL.
[b]Grams.
[c]Time at temperature for gas uptake to cease, hours.
[d]mmol acrylonitrile converted per hour at maximum uptake.
[e]Percent of theoretical.
[f]Molar, based on acrylonitrile.

Examples 5–8 illustrate that in reaction mixtures in which the concentration of acrylonitrile has been increased over a conventional level, i.e., from 63.0 g in a 700 mL reactor charge, the addition of an orthoester allowed yields greater than those observed in Examples 1–4. Thus, a larger amount of cyanopropionaldehyde dimethyl acetal was formed per reactor batch, and reactor productivity was enhanced.

These results show, in contrast to the reactions in Examples 1–4 in which the orthoester was not added and the amount of CPAA product formed per reactor batch actually decreased, addition of the orthoester maintained high reaction rates (k) under conditions of high acrylonitrile concentration and levels of CPAA increased. Also, in contrast, Comparative Examples 1–4 show that when attempting to enhance productivity by operating at higher acrylonitrile concentration but in the absence of the orthoester, one does not obtain more CPAA per reactor batch and one suffers lower reaction rates and therefore incurs longer reaction times. Both factors result in diminished reactor productivity.

TABLE 3-continued

| Example | Acrylonitrile conc[b] | time[c] | $k^d$ const | gas uptake[e] | CPAA grams | Yield[f] CPAA | (CPA) |
|---|---|---|---|---|---|---|---|

[e]percent of theoretical.
[f]Molar, based on acrylonitrile.

Gas chromatographic analysis using the internal standard technique showed that the reactor contained 322 grams of CPAA or more than three times more than was formed using the comparative procedure as illustrated in Comparative Example 1.

What is claimed is:

1. In a process for producing cyanoacetals wherein an α, β-unsaturated nitrile is reacted with carbon monoxide and hydrogen in the presence of a Group 8 metal catalyst, the improvement which resides in effecting the reaction in the presence of a triorganoorthoester or a diorgano ketal.

2. The process of claim 1 wherein the α,β-unsaturated nitrile is selected from the group consisting of acrylonitrile, 2-methylacrylonitrile, 2-n-propylacrylonitrile, 2-ethylacrylonitrile, 2-isopropylacrylonitrile and 2-phenylacrylonitrile.

3. The process of claim 2 wherein the reaction is carried out in the presence of an alcohol having from about 1–30 carbon atoms.

4. The process of claim 3 wherein the unsaturated nitrile is acrylonitrile and the alcohol is a primary or secondary alcohol having from 1–8 carbon atoms.

5. The process of claim 4 wherein the alcohol is selected from the group consisting of methanol, ethanol, isopropyl alcohol, butanol, butan-2-ol; 3-hexanol, ethyidodecanol, ethylene glycol, propylene glycol, cyclohexanol and octanol.

6. The process of claim 3 wherein the triorganoorthoester is represented by the formula [(R'O)$_3$CR"] wherein R' is aliphatic having from 1 to 8 carbon atoms, and R" is hydrogen or C$_{1-8}$ aliphatic or aromatic.

7. The process of claim 3 wherein in the triorganoorthoester represented by the formula [(R'O)$_3$CR"] R' is methyl, ethyl, propyl or butyl and R" is hydrogen, methyl, ethyl, propyl or butyl.

8. The process of claim 7 wherein the ester is selected from the group consisting of trimethyl- orthoformate, triethylorthoformate, tri-n-propylorthoformate, tri-i-propylorthoformate, tri-n-butylorthoformate, tri-sec-butylorthoformate, and tri-i-butylorthoformate.

9. The process of claim 6 wherein from 0.5 to 1.5 moles triorgano ester per mole of alpha, beta-unsaturated nitrile are employed in the reaction.

10. The process of claim 9 where the catalyst contains cobalt.

11. The process of claim 5 where the reaction is carried out in the presence of a dialkyl ketal of the formula [(R'O)$_2$CR"$_2$] wherein R is aliphatic having from 1–8 carbon atoms and R" is C$_{1-8}$ aliphatic or aromatic.

12. The process of claim 11 wherein from 0.5 to 1.5 moles diketal per mole of alpha, beta-unsaturated nitrile are employed in the reaction.

13. The process of claim 12 where the catalyst contains cobalt.

* * * * *